United States Patent [19]

Reynolds, Jr.

[11] Patent Number: 4,702,610
[45] Date of Patent: Oct. 27, 1987

[54] UNDULATING MIXING DEVICE

[76] Inventor: Albert B. Reynolds, Jr., 6-6 Copeley Hill, Charlottesville, Va. 22903

[21] Appl. No.: 935,790

[22] Filed: Nov. 28, 1986

Related U.S. Application Data

[63] Continuation of Ser. No. 724,530, Apr. 18, 1985, abandoned.

[51] Int. Cl.$^4$ .............................................. B01F 11/00
[52] U.S. Cl. ..................................... 366/213; 366/111; 366/208; 366/209; 366/215
[58] Field of Search .................................. 366/110-112, 366/114, 116, 128, 213, 208, 209, 215-217, 210, 211, 602-605, 219, 239

[56] References Cited

U.S. PATENT DOCUMENTS

| 3,985,307 | 10/1976 | Ebbert et al. | 366/602 X |
| 4,118,801 | 10/1978 | Kraft et al. | 366/208 X |
| 4,305,668 | 12/1981 | Bilbrey | 366/208 X |

Primary Examiner—Timothy F. Simone

[57] ABSTRACT

A mixing device and method is provided for stirring solutions by imparting a rotational, undulating motion thereto. The mixing device includes a motor having a speed control which is eccentrically joined to a holding platform. Flexible connectors are attached to the platform to limit its movement and to cause the platform to undulate during its circular motion.

12 Claims, 5 Drawing Figures

UNDULATING MIXING DEVICE

This is a continuation of application Ser. No. 06/724,530 filed 18 Apr. 1985, now abandoned.

BACKGROUND OF THE INVENTION

1. Field of the Invention

The mixing device and method presented herein generally relates to a laboratory instrument and specifically a mixer which operates at low speed for precise blending or stirring.

2. Description of the Prior Art and Objectives of the Invention

In the mixing of most conventional liquid solutions blades or stirrers can be introduced directly therein for agitation. Other solutions and materials as are concerned with here require a high degree of care in handling and in these cases conventionally a beaker or other container which is to be stirred is rotated, shaken or otherwise agitated for the mixing process. In certain laboratory procedures the degree and amount of mixing may be critical and the laboratory technicial must make sure that the blending which is often difficult to regulate is not overly aggressive to prevent damage to one or more of the solution components. For example in certain protein staining processes, a thin sheet of protein containing gelatin is placed within a beaker with a staining solution. The solution is then agitated causing the protein components within the gelatin to absorb the stain. If the agitation is too harsh the thin gelatin composition will shatter and hours of careful preparation and work can be lost. Also, when solutions are mixed having different specific gravities which form stratum, a horizontal mixing motion will not adequately combine the layers. If the horizontal stirring motion is increased sufficiently to encourage mixing, oftentimes air is entrapped within the liquid causing frothing which can be detrimental to the solution and may be unacceptable for a particular laboratory procedure.

With these inadequate and disadvantages known to conventional mixing devices and techniques the present invention was developed and one of its objective is to provide a device for maintaining a controlled rotational undulating motion to a container for gently and effectively mixing the contents therein.

Another objective of the present invention is to provide a sanitary device and method for mixing liquid solutions with other fluids or materials utilizing easily controllable low speeds.

Yet another objective of the present invention is to provide a mixing device which includes a speed control whereby the mixing speed can be precisely adjusted.

Still another objective of the present invention is to provide a mixing device which includes a flexible connector for providing resistance and undulation to the rotational motion.

It is yet another objective of the present invention to provide a device which will eccentrically rotate in a substantially horizontal direction a container for liquids for blending purposes.

Other advantages and objectives of the present invention will become apparent to those skilled in the art as a more detailed description of the invention is revealed below.

SUMMARY OF THE INVENTION

The aforesaid and other objectives of the invention are realized by a mixing device which includes a base upon which an electrical motor having a speed control is mounted. The upright shaft of the motor is joined to an arm which rotates as the motor shaft turns. A holding platform is positioned above the motor and arm which has a central self-centering spherical bearing with an axle extending downwardly therefrom. The axle is attached to the arm in one of several locations therealong depending upon the degree of undulation required. The arm which is attached to the motor shaft and to the axle bearing provides the eccentric motion to the holding platform. As the arm attached to the motor shaft moves in a substantially horizontal circular path, the platform likewise moves in a substantially horizontal circular direction except for the action of flexible connectors which are joined to the platform and to the base. These connectors which may comprise plaistic tubing are of an excess length and are bowed in their relaxed posture due to the extra length. The connectors are flexible and can fully extend during the rotational movement of the holding platform. Also the connectors, when compressed during the rotational movement tend to buckle or bow and upon further compressive force exerted cause the platform to lift in opposition to such compressive force. Thus, as the holding platform moves away from a particular connector in a downward circular direction it will continue in a circular direction toward another or second connector. The platform, as it approaches the second connector will force the second connector to compress. The platform, upon meeting the resistance of the relaxed connector "rides over" the relaxed (bowed) connector causing the platform to temporarily rise and the connector to extend. As the platform passes over the extended connector the connector is relieved of the compressive force and the platform returns to its substantially horizontal circular rotation. As the platform is rectangular in shape with a flexible connector mounted on each corner, the undulating motion (yaw) appears to travel around the perimeter of the platform causing the platform edge to describe a wavelike pattern as the arm circles beneath. As the holding platform is eccentrically attached to the motor, a smooth rotational and undulating method is thereby provided for mixing or stirring purposes. Also, the speed of the motor, by being controllable, allows for an adjustable rotational speed. By the bearing being adjustable as it is attachable to the arm at various points therealong, the degree of undulation can be increased by affixing the bearing inwardly towards the motor shaft and the undulation can be decreased by attaching the bearing farther from the motor shaft until only a horizontal rotational motion is achieved.

DESCRIPTION OF THE PREFERRED EMBODIMENTS

Figure 1:
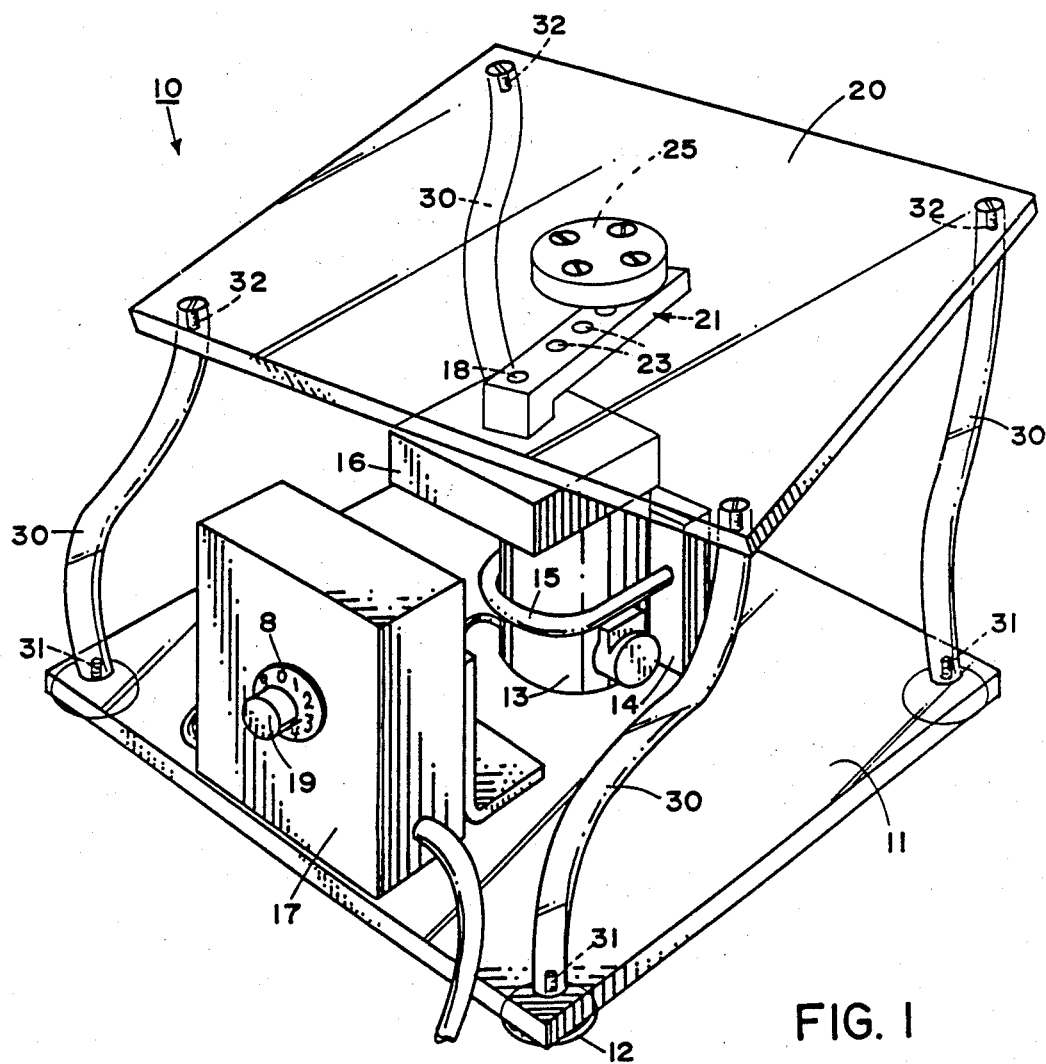
FIG. 1 illustrates a top perspective view of a first embodiment of the invention.

The preferred form of the mixing device of the invention is shown in FIG. 1 and includes a base upon which a fractional horsepower electric motor is mounted and which is regulated by a speed control device also positioned on the base. On each corner of the base flexible connectors made of polyvinyl chloride are attached and extend to affix to four (4) corresponding corners of a container holding platform above. Positioned in the center of the holding platform is a bearing which has extending therefrom a shaft which is connected to an arm connected to the motor shaft. As the motor shaft is positioned substantially over the center of the base, the arm extending therefrom provides an eccentric connection to the bearing positioned in the center of the holding platform.

The preferred method of the invention comprises stirring a liquid which is placed in a beaker or other container on the holding platform, and then by eccentrically rotating the holding platform in a clockwise direction while applying resistance thereto by flexible connectors an undulating rotational motion is generated which will stir the liquid within the container is a controlled, uniform fashion.

DETAILED DESCRIPTION OF THE DRAWINGS

For a more comprehensive explanation of the invention, FIG. 1 demonstrates mixing device 10 having a base 11 which may be formed from a ½ inch rectangular acrylic sheet or other suitable material and includes four (4) cup-like flexible base supports 12 which help secure device 10 on a table or other support during use. Electrical motor 13 may be a fractional horsepower 110 volt AC powered motor although other sizes and types may be employed as required. Motor support plate 14 is affixed to base 11 and as shown in FIG. 1, utilizes U-bolt 15 to hold motor 13 thereto. Gear housing 16 encloses reduction gears which, when used in combination with motor speed control 17 provides motor shaft 18 shown in FIG. 2 with a suitable speed of 0 to 50 rpms. Of course other motor speeds and speed control devices can be employed and in certain laboratory processes rotational mixing speeds may be desired in the 150-250 rpm or higher ranges. Motor speed control device 17 which is commercially available is also affixed to base 11 and includes dial 19 which has a series of numerical indications for precisely setting and controlling the rotational speed of motor shaft 18.

Figure 2:
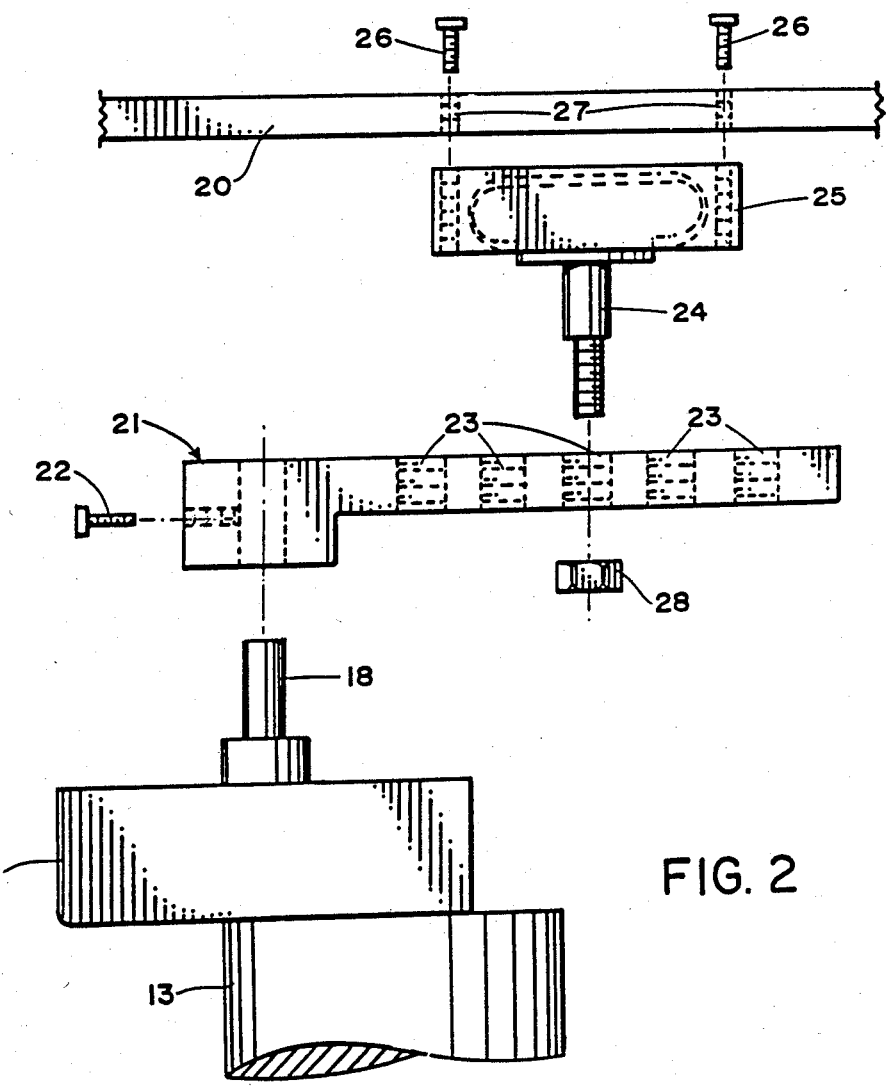
FIG. 2 shows the upper portion of the apparatus of FIG. 1 in exploded fashion.

FIG. 2 demonstrates in exploded fashion the eccentric attachment of motor 13 to container holding platform 20. Arm 21 is positioned on motor shaft 18 and is rigidly positioned by bolt 22. Arm 21 includes a series of axle receiving ports 23 into which bearing axle 24 can be positioned. As eariler explained, the exact position of bearing axle 24 in arm 21 will determine the amount of undulating motion generated by holding platform 20. As further shown, platform bearing 25 is mounted to holding platform 20 by a series of screws 26 which pass through apertures 27 in holding platform 20 which may be formed from a suitable thickness acrylic sheet or other materials. Bearing 25 may be of the self-aligning spherical type and is positioned in the center of rectangularly-shaped holding platform 20. Thus, with motor shaft 18 being positioned at the approximate center of base 11, arm 21 provides an eccentric arrangement whereby the center of platform 20 is not directly over the center of base 11 (FIG. 1). Also, it should be kept in mind that shaft nut 28 only prevents the upward movement of bearing axle 24 and is not tightened against arm 21 as a certain amount of play is necessary to allow for the undulating and rotational movement of platform 20.

Figure 3:
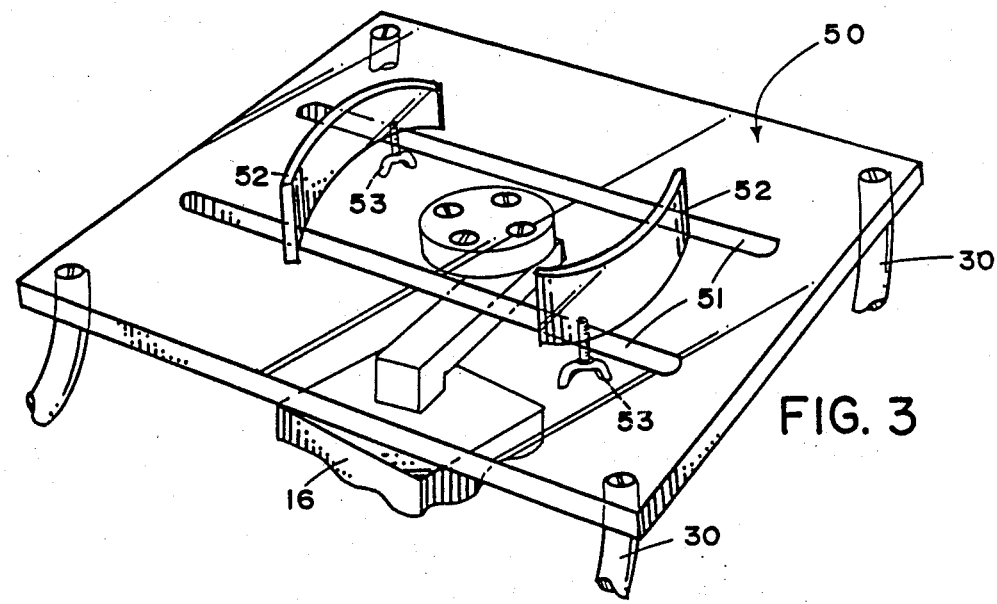
FIG. 3 shows a second embodiment of the holding platform of the invention.

A second embodiment of a rectangular holding platform 50 is shown in FIG. 3 which includes slots 51 for adjustably positioning container holders 52. Container holders 52 are moved to the desired spacing and by tightening the thumb screws 53 container holders 52 can be adjusted to engage a beaker or other container placed therebetween.

As would be understood, the clockwise rotational movement of arm 21 would normally cause a platform or other structure joined thereto to likewise rotate in a clockwise manner of rotating motor shaft 18. However, mixing device 10 includes flexible connector means 30 which provide resistance to the rotational movement of holding platform 20. Flexible connector means 30 are pivotally joined to base 11 and to holding platform 20 at corresponding corners as seen in FIG. 1. Flexible connector means 30 comprise plastic tubing as may be formed from polyethylene, polyvinyl chloride or other suitable materials and are attached by positioning them over base connector shafts 31 and platform connector shafts 32. Connector shafts 31 and 32 may extend approximately ⅜ inch and are of a suitable diameter to allow connector means 30 to easily slip over and pivot therearound. As further shown in FIG. 1, flexible connector means 30 have an excess length and are not generally under tension. As arm 21 rotates, platform 20 attempts to follow the circular movement but platform 20 encounters resistance from at least one of the connector means 30 as holding platform 20 moves toward a particular connector means 30 it rises while connector means 30 fully extends. Holding platform 20 then descends while another portion of platform 20 moves toward another of the flexible connector means 30. As holding platform 20 moves toward a particular connector means 30 the excess length of it (connector means) forces connector means 30 to compress and provide resistance to the movement of platform 20 causing platform 20 to rise over the compressed or partially buckled flexible connector means 30 and connector means 30 extends thereby causing a wave-like undulation motion to platform 20.

Figure 4:
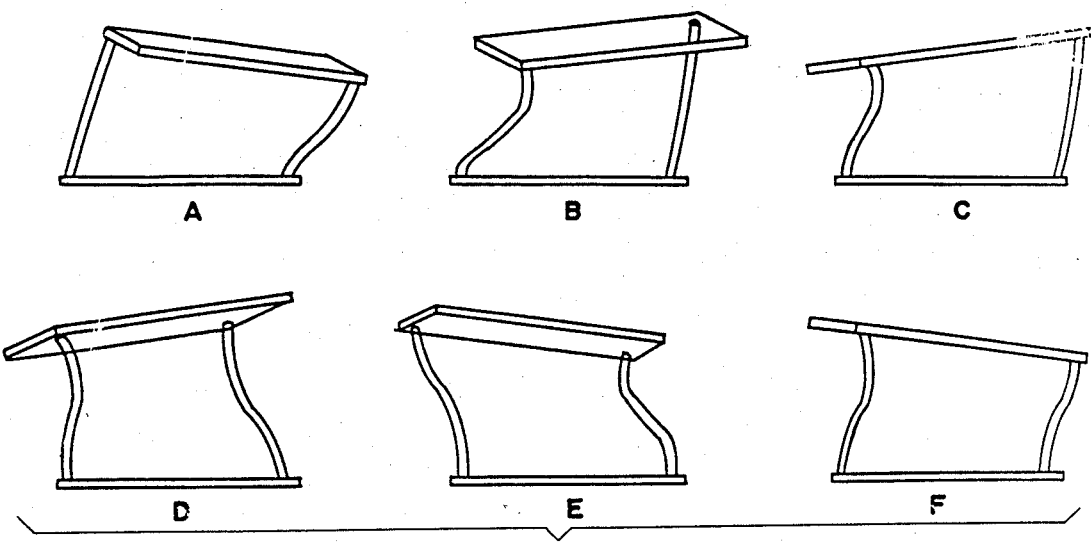
FIG. 4 illustrates the movement of the holding platform as seen from a front elevational view.
Figure 5:
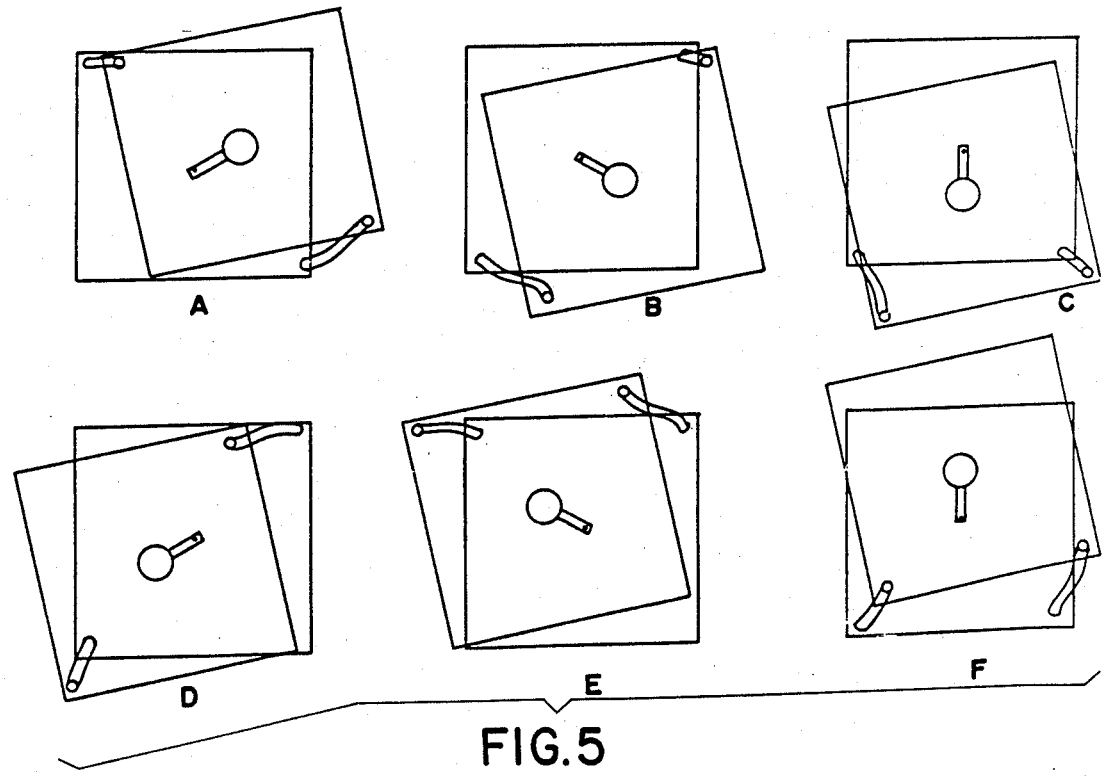
FIG. 5 demonstrates the movement of the holding platform as shown in FIG. 4 as a top plan view.

FIGS. 4 and 5 illustrate the movement of holding platform 20 during a complete revolution of arm 21. FIGS. 4 and 5 are not shown in precise scale but are merely representations of rotational and undulating movement of holding platform 20 with certain connector means displayed in approximate configurations during the rotational movement. FIG. 4(A) corresponds with FIG. 5(A), FIG. 4(B) corresponds to FIG. 5(B) and etcetra whereby FIGS. 4 (A-F) corresponds with FIGS. 5 (A-F). FIG. 4 of course is a front elevational view and FIG. 5 demonstrates a top plan view. As shown in FIG. 4, the rotational movement of platform 20 demonstrates an undulating or wave-like effect as it moves in a clockwise direction whereby the excess length of the connector means causes platform 20 to rise as the resistant forces of the connector means are encountered. For example connector means 42 as shown in FIG. 4(A) is extended whereas connector means 41 is compressed (providing resistance) and partially buckles causing platform 20 to eventually rise above connector means 41 as seen in FIG. 4(C).

As further seen in the schematic representations in FIGS. 4 and 5, holding platform 20 provides an undulating rotational movement which of course can be varied by speed control 17. Also, by moving the bearing axle 24 along arm 21 closer to motor shaft 18, the undulating motion will increase as greater connector means length excesses are encountered. Likewise to decrease the amount of undulation, bearing axle 24 is moved further out arm 21 which causes connector means 30 to assume a straighter posture in their relaxed configuration and therefore less undulation is achieved. This decrease in undulation can be carried out till there is substantially no undulating motion remaining and only rotational motion is then present.

It may be desirable to incorporate a tachometer to measure the rotational speed of motor shaft 18 for particular procedures or a timer may be electrically connected to motor 13 if an automatic timing cycle is desired by using commerically available hardware.

Other changes and modifications can be made to the present invention by those skilled in the art without departing from its scope and the illustrations and examples presented herein are merely for explanatory purposes and are not intended to limit the appended claims.

I claim:

1. A mixing device which provides an undulating motion comprising: a base, a motor mounted on said base, a holding platform, pivoting means, said pivoting means rotatably mounted on said platform, an arm, said arm joined to said pivoting means and to said motor, a flexible connector means, said connector means joined to said base for supporting said platform, said connector means having an excess length and being formed from a flexible material, said length and flexibility such that said connector will bow when said platform is motionless, said connector means joined to said platform whereby said motor rotates said platform and said connector means limits the movement thereof to direct said platform in an undulating orbit.

2. A mixing device as claims in claim 1 wherein said pivoting means comprises a bearing.

3. A mixing device as claimed in claim 2 wherein said bearing comprises a spherical bearing.

4. A mixing device as claimed in claim 1 wherein said motor includes a speed control.

5. A mixing device as claimed in claim 1 and including a plurality of flexible connector means, said connector means joined to said platform and to said base.

6. A mixing device as claimed in claim 3 wherein said bearing has an axle.

7. A mixing device as claimed in claim 2 wherein said arm is adjustably joined to said platform.

8. A mixing device as claimed in claim 1 wherein connector means comprises plastic tubing.

9. A mixing device as claimed in claim 1 wherein said platform is rectangularly shaped and said connector means comprise four (4) tubular members with each of the corners of the rectangularly shaped platform affixed to one of said four (4) connector means.

10. A mixing device for stirring liquids or the like which provides an undulating motion comprising: a base, a motor mounted on said base, a holding platform, pivoting means, said pivoting means rotatably mounted on said platform, an arm, said arm joined to said pivoting means and to said motor to provide eccentric rotation to said platform, a flexible connector means, said connector means having an excess length and being formed from a flexible material, said length and flexibility such that said connector will bow when attached to a motionless platform, said connector means joined to said platform and to said base whereby said motor eccentrically rotates said platform in a substantially horizontal manner while the connector means causes said platform to yaw thereby providing a undulating motion to said platform.

11. A mixing device as claimed in claim 10 and including a speed control attached to said motor.

12. A mixing device as claimed in claim 10 and including a plurality of flexible connector means joined to said platform.

* * * * *